United States Patent [19]

Hardy, Jr.

[11] 4,182,339

[45] Jan. 8, 1980

[54] ANASTOMOTIC DEVICE AND METHOD

[76] Inventor: Thomas G. Hardy, Jr., 350 E. Broad St., Columbus, Ohio 43215

[21] Appl. No.: 906,835

[22] Filed: May 17, 1978

[51] Int. Cl.² ............................................. A61B 17/11
[52] U.S. Cl. ..................................... 128/334 R; 3/1.4
[58] Field of Search ............... 128/334 R, 334 C, 335; 3/1.4, 1.5

[56] References Cited

U.S. PATENT DOCUMENTS

| | | | |
|---|---|---|---|
| 2,428,918 | 10/1947 | Miller | 128/334 R |
| 3,272,204 | 9/1966 | Artandi et al. | 128/334 R |
| 3,564,617 | 2/1971 | Sauvage et al. | 3/1.5 |
| 3,974,835 | 8/1976 | Hardy | 128/334 C |

Primary Examiner—Dalton L. Truluck

[57] ABSTRACT

An anastomotic device and method for receiving the free ends of flexible tubing to be anastomosed, the device has a pliable sleeve with its opposite ends rolled outwardly upon themselves to form relatively firm ring members to engage and secure the free ends of the tubing to be anastomosed, the tubing free ends engaging each other as they are secured to and held by the ring members of the sleeve, the tubing ends being contiguously inverted to enable the ends to grow together permanently.

4 Claims, 6 Drawing Figures

ANASTOMOTIC DEVICE AND METHOD

BACKGROUND, BRIEF SUMMARY AND OBJECTS OF THE INVENTION

This invention relates to devices for surgically anastomosing one hollow or tubular member to another such as, for example, the severed ends of the intestine after resection.

Present medical techniques for joining the severed ends of the intestine include laboriously stitching the severed ends of the vessel together or using stapling instruments which have some inherent disadvantages. The technical difficulties in utilizing such techniques are often numerous because of the inaccessibility of one or both of the ends to be joined, or the time involved for anastomosis.

At present, the ends of the tubular members are usually (a) turned or rolled inwardly to facilitate healing as they rest in a contiguous relationship in the case of suturing techniques, or (b) partially turned or rolled outward in stapling techniques. Since suturing must take place around the circumference of the intestines, many difficulties are sometimes encountered in some areas in holding, gripping, and/or manipulating these elements for proper application of the sutures.

There have been a number of attempts to improve surgical techniques relative to anastomosis. Although there have been significant improvements to assist with the surgical procedures used in anastomeric surgery such as the devices disclosed in U.S. Pat. Nos. 3,496,939 and 3,974,835, these devices are somewhat expensive, complicated, and require very precise and careful handling to be utilized correctly.

It is desirable that a non-permanent connector or a junction device be used to join vessel ends in anastomotic surgery, since a permanent piece of tubing or the like will tend to prevent the changes in diameter which are necessary for the proper functioning of the intestine. Any foreign substance used in anastomotic surgery ideally would disintegrate in a relatively short period of time once the healing of the vessel ends is initiated.

The present invention has been developed to meet the established requirements of anastomotic surgery and provide a safe, relatively inexpensive and easy to use anastomotic device. To summarize the invention, it relates to a soluble anastomotic sleeve which has a certain flexibility so as to provide a surface for securing the abutting ends of tubing. It is formed of a pliable cylindrical sleeve, the ends of which are rolled outwardly upon themselves toward the opposite end to form relatively firm ring members for receiving and securing the free ends of tubular members to be joined. The formed rings are coated with a solution of carnauba wax and stearic acid to produce rigidity, and the sleeve is preferably made of fabric with catgut or similar dissolvable thread to induce satisfactorily timed disintegration.

With the foregoing in mind, it is therefore an object of the present invention to provide an anastomotic device which is soluble in the body fluids and which will disintegrate once in place within a relatively short period of time.

A further object of the present invention is to provide a relatively flexible sleeve to which can be attached the free ends of a hollow or tubular organ.

Yet another object of the present invention is to make possible simple anastomosis in various parts of the body which procedures would normally be quite time consuming, difficult and perhaps impossible.

Yet a further object of the present invention is to provide anastomotic apparatus that is easily produced, relatively inexpensive, and capable of being carried in large quantities by operating rooms for immediate use.

Yet another object of the present invention is to provide an anastomotic sleeve that is constructed of a single piece of pliable material, preferably fabric.

Yet another object of the present invention is to provide an anastomotic sleeve which will hold the ends of the intestine or other similar tubing or the like in close contact with each other and in clamped relation for purposes of forming a permanent bond at the juncture of the contacting ends.

These and other objects of the present invention will become more apparent after consideration of the following detailed specification taken in conjunction with the accompanying drawings wherein like characters of reference designated like parts throughout the several views.

DETAILED DESCRIPTION OF THE INVENTION

Figure 1:
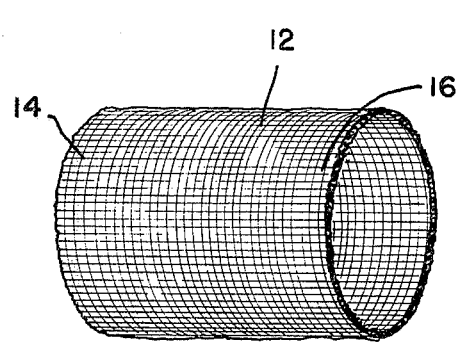
FIG. 1 is a perspective view of the pliable unitary cylindrical sleeve comprising the primary element of the present invention.
Figure 2:
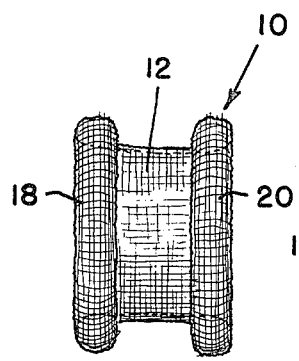
FIG. 2 is a side elevational view of the anastomotic device comprising the present invention showing opposite ends of the sleeve of FIG. 1 rolled outwardly upon themselves to form relatively firm ring members which are coated with a material to promote rigidity.
Figure 3:
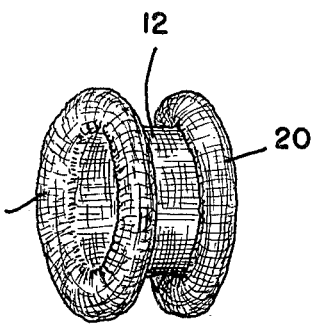
FIG. 3 is a perspective view of the anastomotic device shown in FIG. 2.
Figure 4:
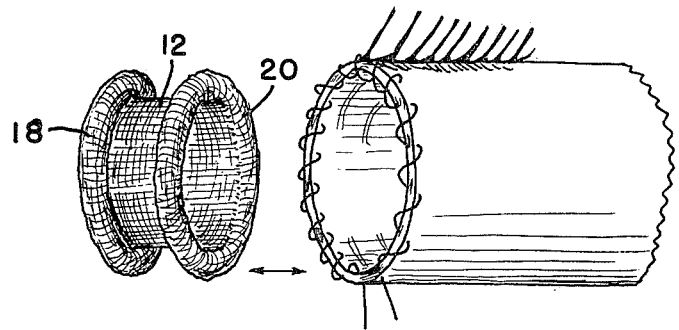
FIG. 4 is a perspective view of the anastomotic device forming the present invention functionally displaced from the free end of a tubular member to be attached thereto, the tubular member having a purse string suture secured to its end to enable attachment to a ring member of the anastomotic device.

Referring now to the drawings and particularly to FIG. 2, an anastomotic device is shown generally as 10. The device is formed from a pliable unitary cylindrical sleeve 12 (FIG. 1) having first and second ends 14 and 16 each of which are rolled outwardly upon themselves toward the opposing end to form relatively firm ring members 18 and 20.

The unitary cylindrical sleeve 12 is pliable because, in preferred form, it is formed of fabric. It has been found advantageous to knit a tubular sleeve on conventional knitting equipment such as the Dubied (Switzerland) 12 cut, 72 needle (2 bank) machine, model NHF4 (not shown). Such machines have been commercially available for a number of years. While conventional knitting equipment can be used to form the cylindrical sleeve, other fabric-forming techniques are quite acceptable for producing the device in useable form.

It is necessary that the sleeve 12 be formed in a manner so that it will disintegrate in a relatively short period of time once healing of the vessel ends begins. For that reason, it has been found advantageous to use as fabric-forming thread, 4–0 Chromic catgut, a substance having predictable destructibility in body fluids. In addition, the formed rings 18 and 20 are preferably coated with a solution of carnauba wax and stearic acid to add rigidity, a quite satisfactory solution of such substances being approximately 62% carnauba wax and 38% stearic acid.

Figure 5:
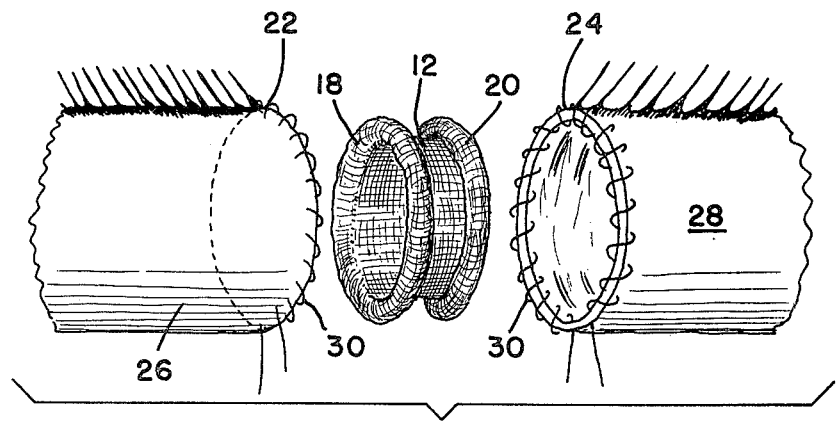
FIG. 5 is a perspective view similar to FIG. 4 except that a second tubular member free end is functionally displaced from the opposite side of the first tubular member free end carrying a purse string suture for attachment to the other ring member of the anastomotic device.

Complete utilization of the anastomotic device is best illustrated in FIG. 5. The free ends 22 and 24 of two tubular members 26 and 28 are stitched with a purse string suture 30. Use of this suture permits engaging the very edge of the free end of the vessel wall so that the suturing material can be pulled and the vessel end contracted much in the way the top of a purse or string-closed bag is manipulated. The ends 22 and 24 are then pulled over ring members 18 and 20 (FIG. 5) so that as the purse string suture is tightened, the ends 22 and 24 of the vessels 26 and 28 turn inwardly over ring members 18 and 20 and thereby become contiguously inverted to enable themselves to grow together permanently.

Figure 6:
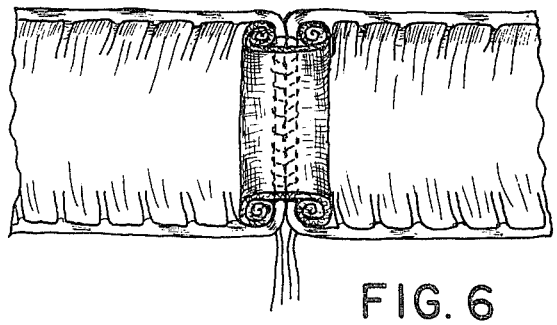
FIG. 6 is a side elevational sectional view of the anastomotic device comprising the present invention holding together two free ends of a severed intestine for subsequent coupling.

FIG. 6 illustrates a completed inverted serosa-to-serosa anastomosis, the anastomotic device insitu in the lumen of the bowel. A purse string suture is visible and illustrates the technique for contiguously inverting the ends of the bowel members to foster immediate healing and permanent junction.

It is to be understood that the anastomotic device, whether it be formed of fabric or other material, is made of a composite material which can be designed to disintegrate in a given period of time. The present invention offers many advantages over conventional anastomotic devices and permits simple, rapid anastomosis in difficult areas. For example, it permits a simple anastomosis in a low rectosigmoid anastomosis which would ordinarily be quite time consuming and difficult, or impossible, in those cases necessitating a colostomy.

It will be therefore apparent that the invention is comprised basically of a pliable cylindrical sleeve which may take the form of the embodiment described herein. However, the invention in its broader aspects is not limited to this specific embodiment herein shown and described, but departures may be made therefrom within the scope of the accompanying claims without departing from its principals and without sacrificing its chief advantages.

What is claimed is:

1. An anastomosis device for use in the surgical joining of the free ends of two tubular members to be anastomosed as the tubular members have portions retained in abutting relation upon said coupling device by purse string sutures, said anastomosis device comprising a pliable, unitary cylindrical sleeve having a central portion and first and second ends, each of which are rolled outwardly upon themselves toward the opposing ends to form a pair of relatively firm ring members in spaced relation upon said central portion, said cylindrical sleeve being of knit fabric, and having said spaced ring members coated with a rigidity promoting material, said knit fabric being at least partially formed of yarn made of dissolvable material, said ring members being spaced apart a prescribed distance for receiving therebetween the inturned free ends of the tubular members as they extend over the ring members from positions generally parallel with said central unrolled portion and retained in abutting relation generally perpendicular to said cylindrical sleeve central unrolled portion by purse string sutures enabling the two tubular members to grow together.

2. The device as claimed in claim 1 wherein said coating is approximately 62% carnauba wax and 38% stearic acid.

3. The device as claimed in claim 1 wherein said dissolvable material is catgut.

4. A method of performing intestinal anastomotic surgery utilizing a pliable cylindrical fabric sleeve knit of dissolvable yarn, the ends of which are rolled outwardly upon themselves toward the opposite ends and coated with a rigidity promoting material to form relatively firm, spaced ring members at each sleeve end comprising the steps of: positioning the free end of one of two tubular tissue members to be joined over one of the sleeve ring members and directing the end portion inwardly radially of the sleeve and between the spaced rings; tying the free end over the ring member; positioning the free end of the other tubular tissue member to be joined over the second ring member and directing the end portion inwardly radially of the sleeve between the spaced rings and in abutting relation with the other tubular tissue member; and tying the free end over the ring member so that both free tissue member ends are positioned between the ring members of the cylindrical sleeve and to each other to facilitate healing.

* * * * *